United States Patent [19]

Rowlands et al.

[11] Patent Number: 4,762,840

[45] Date of Patent: Aug. 9, 1988

[54] PYRIMIDO[2,1-B]BENZOTHIAZOLES HAVING ANTIALLERGIC ACTIVITY

[75] Inventors: David A. Rowlands, Malmesbury; Julian M. C. Golec, Swindon; Saroop S. Matharu, Cricklade; Peter W. Hairsine, Swindon, all of England

[73] Assignee: Roussel Uclaf, Paris, France

[21] Appl. No.: 892,771

[22] Filed: Jul. 31, 1986

Related U.S. Application Data

[63] Continuation-in-part of Ser. No. 700,446, Feb. 11, 1985, abandoned.

[30] Foreign Application Priority Data

Feb. 13, 1984 [GB] United Kingdom ............... 8403739
Jul. 31, 1985 [GB] United Kingdom ............... 8519261

[51] Int. Cl.⁴ ................... A61K 31/505; C07D 513/04
[52] U.S. Cl. ................... 514/267; 514/233.2; 544/115; 544/135; 544/250; 548/162; 560/20; 560/43; 562/433; 562/434; 558/388
[58] Field of Search ............... 514/231, 267; 544/115, 544/250

[56] References Cited

U.S. PATENT DOCUMENTS

| | | | |
|---|---|---|---|
| 3,538,086 | 11/1970 | Mair et al. ...................... | 544/250 X |
| 3,813,360 | 5/1974 | Evans ............................... | 544/250 X |
| 4,041,163 | 8/1977 | Bidra et al. ...................... | 544/250 X |
| 4,223,031 | 9/1980 | Covington et al. ................ | 544/250 |
| 4,232,024 | 11/1980 | Winter et al. ..................... | 514/267 |
| 4,423,048 | 12/1983 | Kadin ............................... | 514/267 X |
| 4,548,938 | 10/1985 | Kennis et al. ..................... | 514/258 |

FOREIGN PATENT DOCUMENTS 0153230 8/1985 European Pat. Off. .

OTHER PUBLICATIONS

Antaki, et al., Chemical Abstracts, vol. 45, 9061e (1951).
Alaimo, J. Heterocyclic Chem., vol. 10, No. 5, pp. 769-772 (1973).

Primary Examiner—Donald G. Daus
Assistant Examiner—Diana G. Rivers
Attorney, Agent, or Firm—Bierman and Muserlian

[57] ABSTRACT

Novel pyrimido[2,1-b]benzothiazoles of the formula

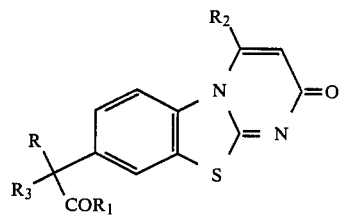

wherein R and $R_3$ are individually selected from the group consisting of hydrogen and alkyl of 1 to 6 carbon atoms or taken together with the carbon to which they are attached form a cycloalkyl of 3 to 6 carbon atoms, $R_1$ is selected from the group consisting of hydroxy, alkoxy of 1 to 12 carbon atoms, cycloalkyl of 7 to 12 carbon atoms, and

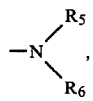

$R_5$ and $R_6$ are individually selected from the group consisting of hydrogen and alkyl of 1 to 6 carbon atoms or taken together with the nitrogen form piperidino or morpholino, $R_2$ is selected from the group consisting of hydrogen, alkyl of 1 to 6 carbon atoms, alkoxycarbonyl of 2 to 7 carbon atoms, cycloalkyl of 3 to 6 carbon atoms, heteroaryl, aralkyl and optionally substituted aryl with at least one substituent selected from the group consisting of halogen, nitro, and alkyl and alkoxy of 1 to 6 carbon atoms and their salts with non-toxic, pharmaceutically acceptable acids and bases having antiallergic activity.

34 Claims, No Drawings

PYRIMIDO[2,1-B]BENZOTHIAZOLES HAVING ANTIALLERGIC ACTIVITY

PRIOR APPLICATION

This application is a continuation-in-part of our copending U.S. patent application Ser. No. 700,446, filed Feb. 11, 1985, now abandoned.

STATE OF THE ART

British Pat. No. 1,345,148 describes compounds structurally related to the compounds of formula I having different pharmacological activities.

OBJECTS OF THE INVENTION

It is an object of the invention to provide the novel compounds of formula I and their non-toxic, pharmaceutically acceptable acid addition salts, a novel process for their preparation and novel intermediates.

It is another object of the invention to provide novel antiallergic compositions and a novel method of treating allergies in warm-blooded animals.

These and other objects and advantages of the invention will become obvious from the following detailed description.

THE INVENTION

The novel compounds of the invention are selected from the group consisting of pyrimido[2,1-b]benzothiazoles of the formula

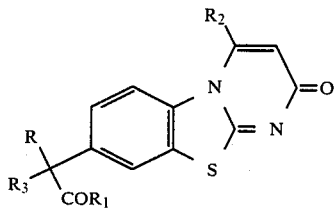

I wherein R and $R_3$ are individually selected from the group consisting of hydrogen and alkyl of 1 to 6 carbon atoms or taken together with the carbon to which they are attached form a cycloalkyl of 3 to 6 carbon atoms, $R_1$ is selected from the group consisting of hydroxy, alkoxy of 1 to 12 carbon atoms, cycloalkoxy of 7 to 12 carbon atoms and

$R_5$ and $R_6$ are individually selected from the group consisting of hydrogen and alkyl of 1 to 6 carbon atoms or taken together with the nitrogen form piperidino or morpholino, $R_2$ is selected from the group consisting of hydrogen, alkyl of 1 to 6 carbon atoms, alkoxycarbonyl of 2 to 7 carbon atoms, cycloalkyl of 3 to 6 carbon atoms, heteroaryl, aralkyl and optionally substituted aryl with at least one substituent selected from the group consisting of halogen, nitro and alkyl and alkoxy of 1 to 6 carbon atoms and their salts with non-toxic, pharmaceutically acceptable acid and bases.

Examples of alkyl of 1 to 6 carbon atoms are methyl, ethyl, n-propyl, isopropyl, butyl, isobutyl, pentyl and hexyl and examples of alkoxy of 1 to 12 carbon atoms are methoxy, ethoxy, propoxy, isopropoxy, butoxy, pentoxy and hexyloxy, heptyloxy, octyloxy, nonyloxy, and decyloxy. Examples of cycloalkyl of 3 to 6 carbon atoms are cyclopropyl, cyclobutyl and cyclohexyl and examples of aralkyl of 7 to 12 carbon atoms are benzyl and phenethyl. Examples of cycloalkoxy of 7 to 12 carbon atoms are 1-methylcyclohexyloxy and 1-adamantyloxy. Examples of aryl of 6 to 12 carbon atoms are phenyl and naphthyl and examples of alkoxycarbonyl of 2 to 7 carbon atoms are methoxycarbonyl, ethoxycarbonyl and propoxycarbonyl. The halogens may be chlorine, bromine or fluorine. The heteroaryl groups may have one or more heteroatoms such as sulfur in the aryl ring and may be 2-thienyl, for example.

When $R_1$ is —OH, the compounds of formula I are acidic in character and can form salts with bases of metals such as alkali metals like sodium, potassium and lithium, alkaline earth metals such as calcium or metals such as aluminum and magnesium or with nitrogen bases such as ammonium hydroxide or with amines such as tromethamine, triethanolamine, lysine and arginine.

When $R_1$ is cycloalkoxy or alkoxy or

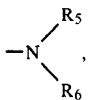

the compounds of formula I have a basic character and can form acid addition salts with inorganic acids such as hydrochloric acid, hydrobromic acid, hydriodic acid, nitric acid, sulfuric acid or phosphoric acid or organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methanesulfonic acid and arylsulfonic acids such as benzene sulfonic acid.

Among the preferred compounds of the invention of formula I are those wherein R and/or $R_3$ are hydrogen, methyl or ethyl and those wherein R and $R_3$ are hydrogen, methyl or ethyl and $R_2$ is hydrogen, alkyl of 1 to 6 carbon atoms, methoxycarbonyl or phenyl optionally substituted with at least one member of the group consisting of halogen, methyl, methoxy and nitro and their non-toxic, pharmaceutically acceptable salts.

As examples of especially preferred compounds of the invention mention may be made of those compounds of formula I and acid addition salts thereof wherein one or both of R and $R_3$ is hydrogen or methyl or ethyl, $R_2$ is phenyl and $R_1$ is 1-methylcyclohexyloxy or 1-adamantyloxy.

Examples of specific preferred compounds of formula I are ethyl 2-oxo-4-phenyl-2H-pyrimido[2,1-b]benzothiazole-8-acetate; ethyl 2-oxo-4-(p-methoxyphenyl)-2H-pyrimido[2,1-b]benzothiazole-8-acetate; ethyl 2-oxo-4-(o-chlorophenyl)-2H-pyrimido[2,1-b]benzothiazole-8-acetate; ethyl α-methyl-2-oxo-4-phenyl-2H-pyrimido[2,1-b]benzothiazole-8-acetate; ethyl α-methyl-2-oxo-4-(p-chlorophenyl)-2H-pyrimido[2,1-b]benzothiazole-8-acetate; ethyl α-ethyl-2-oxo-4-phenyl-2H-pyrimido[2,1-b]benzothiazole-8-acetate; 1-methylcyclohexyl α-methyl-2-oxo-4-phenyl-2H-pyrimido[2,1-b]benzothiazole-8-acetate and 1-adamantyl α-methyl-2-oxo-4-phenyl-2H-pyrimido-[2,1-b]benzothiazole-8-acetate; and their non-toxic, pharmaceutically acceptable salts.

The novel process of the invention for the preparation of compounds of formula I wherein $R_1$ is hydroxy or alkoxy and salts thereof comprises reacting a compound of the formula

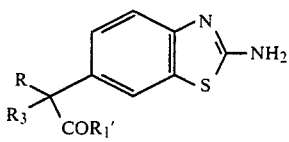   II wherein R and $R_3$ have the above definitions and $R_1'$ is hydroxy or alkoxy of 1 to 6 carbon atoms, preferably alkoxy, with a compound of the formula $$R_2-C\equiv C-CO_2R_4 \qquad III$$

wherein $R_2$ has the above definition and $R_4$ is alkyl, preferably alkyl of 1 to 3 carbon atoms, followed if desired by the isolation of, and/or formation of a salt of, the compound of formula I thus obtained.

Compounds of formula I wherein $R_1$ is

may be prepared by reaction of a compound of formula I wherein $R_1$ is hydroxy with a compound of the formula

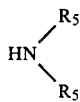   B wherein $R_5$ and $R_6$ have the above definitions in the presence of 1,1'-carbonyldiimidazole.

The compounds of formula I wherein $R_1$ is hydroxy are also useful as intermediates for the preparation of other compounds of the invention, for example by esterification by reaction with an alcohol of the formula $$HO-R_1'' \qquad IV$$

wherein $R_1''$ is alkyl of 1 to 6 carbon atoms.

Similarly, compounds of formula I wherein $R_1$ is alkoxy may also be used as intermediates in the preparation of other compounds of the invention, for example by the following processes which also constitute further features of the invention:

(i) transesterifying a compound of formula I wherein $R_1$ is alkoxy of 1 to 6 carbon atoms with an alcohol of the formula $$HO-R_1'' \qquad IV$$

wherein $R_1''$ is a different alkyl of 1 to 6 carbon atoms and (ii) deesterifying a compound of formula I wherein $R_1$ is alkoxy of 1 to 6 carbon atoms to obtain a compound of formula I wherein $R_1$ is hydroxy.

The said processes of the invention are preferably carried out in the following manner: The reaction of 2-aminobenzothiazole of formula II with the propiolate of formula III may be, and when $R_2$ is hydrogen preferably is, effected under reflux and in the presence of an alcohol such as ethanol and a catalyst such as palladium. However, when in the propionate of formula III, $R_2$ is other than hydrogen, the reaction is preferably effected with heating, e.g. to 100°–180° C. and in the absence of a solvent. The deesterification of a compound of formula I wherein $R_1$ is alkoxy is suitably effected with the use of a weak base such as potassium carbonate.

Salts with metal ions or nitrogen bases of compounds of formula I wherein $R_1$ is hydroxy may be prepared by reacting the said compounds of formula I with an appropriate base such as an alkali metal, alkaline earth metal or nitrogen bases. Salts with acids of compounds of formula I wherein $R_1$ is an alkoxy or $-NR_5R_6$ may be prepared by reacting the same compounds of formula I with an appropriate acid.

The antiallergic compositions of the invention are comprised of an antiallergically effective amount of at least one compound of formula I and their non-toxic, pharmaceutically acceptable salts and an inert pharmaceutical carrier or excipient. The compositions may be in the form of tablets, dragees, gelatin capsules, granules, suppositories, syrups, aerosols, creams, ointments and injectable solutions or suspensions.

The antiallergic compositions of the invention are useful for the treatment of allergic asthma and asthmatiform bronchitis of allergic origin.

The preferred compositions of the invention are those wherein R and/or $R_3$ are hydrogen, methyl or ethyl and those wherein R and $R_3$ are hydrogen, methyl or ethyl and $R_2$ is hydrogen, alkyl of 1 to 6 carbon atoms, methoxycarbonyl or phenyl optionally substituted with at least one member of the group consisting of halogen, methyl, methoxy and nitro and their non-toxic, pharmaceutically acceptable salts.

Examples of specific preferred compounds of formula I are ethyl 2-oxo-4-phenyl-2H-pyrimido[2,1-b]benzothiazole-8-acetate; ethyl 2-oxo-4-(p-methoxyphenyl)-2H-pyrimido[2,1-b]benzothiazole-8-acetate; ethyl 2-oxo-4-(o-chlorophenyl)-2H-pyrimido[2,1-b]benzothiazole-8-acetate; ethyl α-methyl-2-oxo-4-phenyl-2H-pyrimido[2,1-b]benzothiazole-8-acetate; ethyl α-methyl-2-oxo-4-(p-chlorophenyl)-2H-pyrimido[2,1-b]benzothiazole-8-acetate; ethyl α-ethyl-2-oxo-4-phenyl-2H-pyrimido[2,1-b]benzothiazole-8-acetate; 1-methylcyclohexyl α-methyl-2-oxo-4-phenyl-2H-pyrimido[2,1-b]benzothiazole-8-acetate; and 1-adamantyl α-methyl-2-oxo-4-phenyl-2H-pyrimido[2,1-b]benzothiazole-8-acetate; and their non-toxic, pharmaceutically acceptable salts.

Examples of suitable excipients are talc, gum arabic, lactose, starch, magnesium stearate, cocoa butter, aqueous or non-aqueous vehicles, animal or vegetable fats, paraffin derivatives, glycols, and various wetting, dispersing or emulsifying agents and/or preservatives.

The novel method of the invention to treat allergies in warm-blooded animals, including humans, comprises administering to warm-blooded animals an antiallergically effective amount of at least one compound of formula I and their non-toxic, pharmaceutically acceptable salts. The compounds may be administered orally, rectally, topically or parenterally. The usual daily dose is 0,01 to 14 mg/kg depending on the condition treated, the specific compound and the method of administration.

Some of the compounds of formula II are known and are described in Sawhney et al [Ind. J. Chem., Vol. 16B, p. 605 (1978)] and in German Offenlegungsschrift No.

2,015,158, U.S. Pat. No. 3,656,958 and European Patent Application Publication No. 17543A. However certain compounds of formula II are novel.

The novel compounds of the invention of formula II are

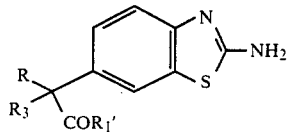

wherein R, $R_1'$ and $R_3$ have the above definitions with the proviso that when $R_1'$ is hydroxy, $R_3RC<$ is other than $CH_3CH<$ or $>CH_2$ and that when $R_1'$ is ethoxy, $R_3RC<$ is other than a methylene group which are useful as intermediates in the preparation of compounds of formula I.

The compounds of formula II wherein R and $R_3$ are hydrogen which are not known from the literature may be prepared from p-nitrophenyl-acetic acid according to the following reaction scheme:

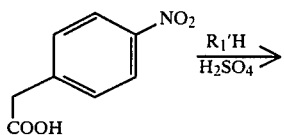

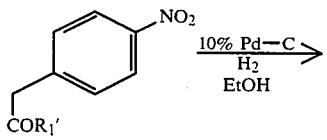

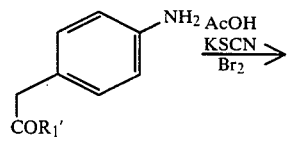

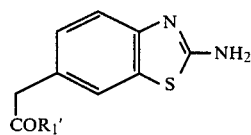

wherein $R_1'$ is alkoxy of 1 to 6 carbon atoms.

Compounds of formula II which are not known from the literature may also be prepared from α-phenyl aldehydes by the following reaction schemes:

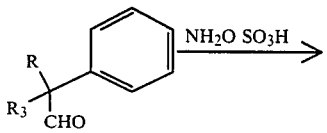

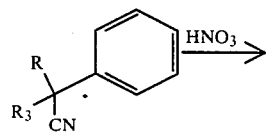

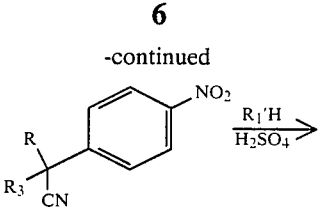

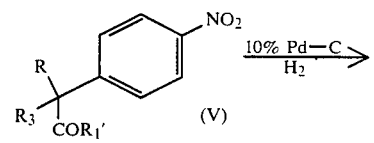

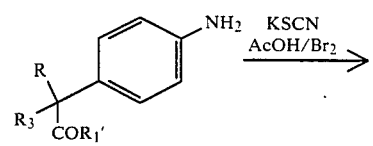

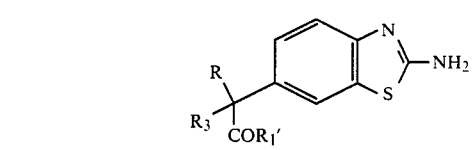

wherein $R_1'$ is alkoxy of 1 to 6 carbon atoms.

When compounds in which R and $R_3$ are alkyl of 1 to 6 carbon atoms are to be prepared, it is preferable to prepare the intermediate of formula V in the above reaction scheme by alkylation of an intermediate of formula VI

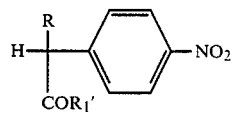

VI wherein R is alkyl of 1 to 6 carbon atoms and $R_1'$ is alkoxy of 1 to 6 carbon atoms using for example an alkyl iodide $R_3I$ and a base such as lithium diisopropylamide or lithium N-isopropylcyclohexylamide in a suitable solvent such as tetrahydrofuran. The preparation of the intermediates of formula VI themselves is described below.

The compounds of formula II wherein $R_3RC<$ is $CH_3CH<$ may in an alternative process be prepared from α-phenyl-propionic acid by the following reaction scheme:

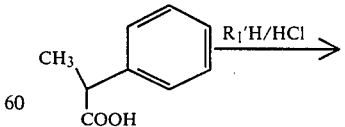

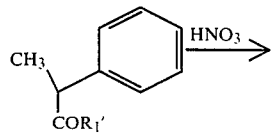

-continued

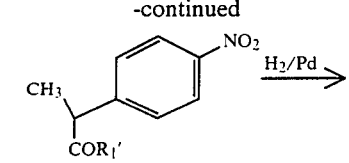

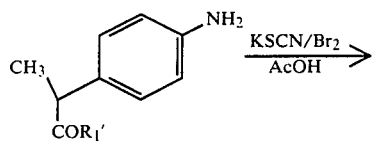

wherein $R_1'$ is alkoxy of 1 to 6 carbon atoms.

The compounds of formula II wherein $R_3$ or R is hydrogen may also be prepared from 1-chloro-4-nitrobenzene by the following reaction scheme (the early stages of which are developed from the reaction scheme of Hino et al [J. Med. Chem., Vol. 26, P. 222-226 (1983))]

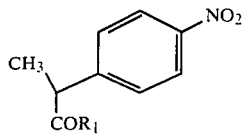

(wherein $R_1$ is as hereinbefore defined) may be prepared from 2-(p-nitrophenyl)propionic acid by the following reaction scheme:

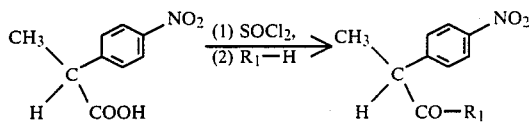

The compounds of formula V wherein R, $R_2$ and $R_3$ are as defined hereinbefore and $R_1''$ represents a hydroxy radical or a $C_{1-6}$ alkoxy group may be prepared according to the process described in European Patent Application No. 0,153,230.

Compounds of formula I, while being compounds of the invention in their own right, may also be used as intermediates for the preparation of further compounds of the invention, for example by transesterification of a compound of formula I wherein $R_1$ is straight-chained,

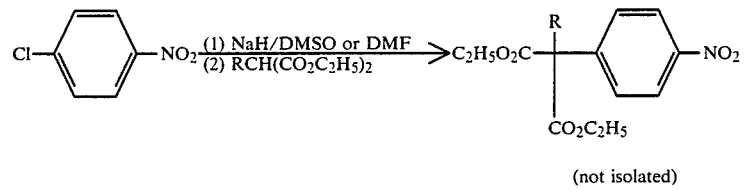

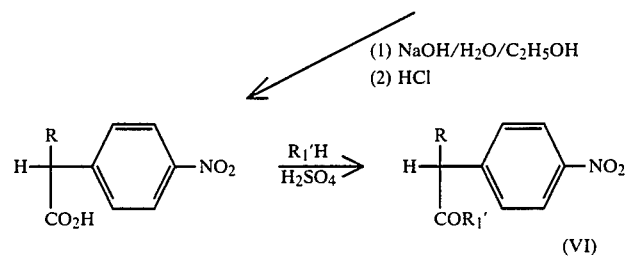

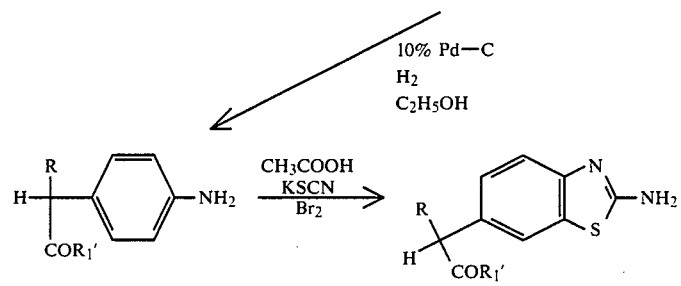

wherein R is hydrogen or alkyl of 1 to 6 carbon atoms, preferably methyl or ethyl, and $R_1'$ is alkoxy of 1 to 6 carbon atoms.

Alternatively, the compounds of formula branched or cyclic alkoxy of 7 to 12 carbon atoms with an alcohol of the formula $$H—R_1'  \qquad \text{IV}$$

wherein $R_1'$ is a different straight-chained, branched or cyclic alkoxy group of 7 to 12 carbon atoms.

Similarly, compounds of formula I may be prepared by transesterification of a compound of formula V

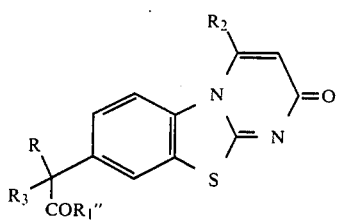

wherein $R_1''$ is alkoxy of 1 to 6 carbon atoms with an alcohol of the formula $$H—R_1 \qquad VI$$

wherein $R_1$ is a straight-chained, branched or cyclic alkoxy of 7 to 12 carbon atoms.

Compounds of formula I may also be prepared by esterification, whereby a compound of formula V wherein $R_1''$ is hydroxy group is reacted with an alcohol of formula $$H—R_1 \qquad VI$$

wherein $R_1$ is as hereinbefore defined.

In the following examples there are described several preferred embodiments to illustrate the invention. However, it is to be understood that the invention is not intended to be limited to the specific embodiments.

EXAMPLE 1

Ethyl 2-oxo-2H-pyrimido[2,1-b]benzothiazole-8-acetate

A stirred mixture of 5 g of ethyl 2-aminobenzothiazole-6-acetate [prepared according to Sawhney et al., Ind J. Chem., Vol. 16B p. 605 (1978)], 1.95 g of methyl propiolate and 30 ml of ethanol was heated under reflux for 2 hours and the mixture was allowed to cool. The crude product was collected and then recrystallized from n-butyl alcohol to obtain 2.88 g of ethyl 2-oxo-2H-pyrimido[2,1-b]benzothiazole-8-acetate as yellow needles (48% yield).

EXAMPLE 2

Ethyl 2-oxo-2H-pyrimido[2,1-b]benzothiazole-8-α-methylacetate

STEP A: 2-amino-α-methyl benzothiazole-6-acetonitrile 27.4 g of bromine in 87.5 ml of 95% v/v acetic acid were added dropwise to a stirred mixture of 25 g of 2-(p-aminophenyl)propionitrile [British Pat. No. 1,198,212], 66.8 g of potassium thiocyanate and 300 ml of 95% v/v acetic acid at ambient temperature. The mixture was then stirred at 50° C. for a further 2 hours before being poured into 1.5 liters of water. The solution obtained was filtered through celite and sodium bicarbonate was then added to the filtrate until no further precipitation occurred. The precipitate was collected and crystallized from methanol/water to give 19.4 g (56%) of 2-amino-α-methyl benzothiazole-6-acetonitrile as yellow prisms melting at 165.1° C.

$IR_{max}$ 3400, 3280 ($NH_2$), 2220 (CN), 1640, 1540, 1460 and 815 cm$^{-1}$

Analysis: $C_{10}H_9N_3S$: Calculated: %C 59.09; %H 4.46; %N 20.67; %S 15.77; Found: C 58.76; H 4.42; N 20.74; S 15.74

STEP B: Ethyl 2-amino-α-methylbenzothiazole-6-acetate

A stirred solution of 10 ml of 95% ethanol, 10 g of conc. $H_2SO_4$, and 0.5 g of the compound of Step A above was heated at reflux for 20 hours and the mixture was then cooled, diluted with water and the ethanol was evaporated off. The resulting solution was neutralized with sodium bicarbonate to obtain a solid which was collected and crystallized from methanol/water to obtain 0.38 g (61%) of ethyl 2-amino-α-methylbenzothiazole-6-acetate as off-white needles melting at 146° C.

$IR_{max}$ 3370, 3120, 2980, 1710, (ester CO), 1640, 1540, 1470, 1375, 1330, 1295 and 1225 cm$^{-1}$ Analysis: $C_{12}H_{14}N_2O_2S$: Calculated: %C 57.60; %H 5.65; %N 11.20; %S 12.80; Found: C 57.65; H 5.65; N 11.20; S 12.95

STEP C: ethyl 2-amino-α-methylbenzothiazole-6-acetate

Using the method of Example 1, ethyl 2-amino-α-methylbenzothiazole-6-acetate and methyl propiolate were reacted at reflux for 17 hours to obtain a 42% yield of ethyl 2-oxo-2H-pyrimido[2,1-b]benzothiazole-8-α-methylacetate.

The said starting material was also prepared by dissolving 154.6 g of ethyl 2-(p-aminophenyl)propionate [Arzneim. Forsch, Vol. 23, p. 1090 (1973)] in 95% acetic acid and 261 g of potassium isothiocyanate were added with stirring. A solution of 149.4 g of $Br_2$ in 750 ml of 95% acetic acid was then added dropwise at 18°–25° C. over 2 hours and the mixture was stirred for an extra half hour, then poured into 8 liters of water. The mixture was filtered through celite and then neutralized to pH 5–6 using 6+ liters of 20% $Na_2CO_3$ solution. The product was then extracted with $CH_2Cl_2$ and the organic layer was separated, washed with water, dried over $MgSO_4$ and finally filtered and evaporated to dryness. The crude product was dissolved in 300 ml of hot ethyl acetate and an equal volume of petroleum ether (40°–60° C.) was added. On cooling, cream colored crystals were formed which were filtered off, washed with ethyl acetate/petroleum ether and dried to obtain 97 g (48.5% yield) of the ethyl 2-amino-α-methylbenzothiazole-6-acetate melting at 146° C. A second crop of 29 g was obtained from the mother liquors for a total yield 63%.

EXAMPLE 3

Ethyl 2-oxo-4-phenyl-2H-pyrimido[2,1-b]benzothiazole-8-acetate

A stirred mixture of 5 g of ethyl 2-aminobenzothiazole-6-acetate and 6 g of ethyl phenylpropiolate was heated at 200° C. in an oil bath for 1 hour and the crude mixture was then purified on a column of 200 g of silica using $CHCl_3$ as eluant. The product obtained was highly colored and was crystallized from $CHCl_3$ and crystallized from ethanol to obtain 1.99 g (26% yield) of ethyl 2-oxo-4-phenyl-2H-pyrimido[2,1-b]benzothiazole-8-acetate as orange plates.

EXAMPLE 4

Methyl 2-oxo-4-phenyl-2H-pyrimido[2,1-b]benzothiazole-8-acetate

Using the method of Example 1 with corresponding compound of formula II wherein $R_1'$ is methoxy and ethyl phenylpropiolate (compound of formula III), methyl 2-oxo-4-phenyl-2H-pyrimido[2,1-b]benzothiazole-8-acetate was obtained.

EXAMPLE 5 n-Propyl 2-oxo-4-phenyl-2H-pyrimido[2,1-b]benzothiazole-8-acetate

Using the method of Example 3 with corresponding compound of formula II wherein $R_1'$ is n-propoxy and ethyl phenylpropiolate (compound of formula III), n-propyl 2-oxo-4-phenyl-2H-pyrimido[2,1-b]benzothiazole-8-acetate was obtained.

EXAMPLE 6

Isopropyl 2-oxo-4-phenyl-2H-pyrimido[2,1-b]benzothiazole-8-acetate

Using the procedure of Example 3 with corresponding compound of formula II wherein $R_1'$ is isopropoxy and ethyl phenylpropiolate (compound of formula III), isopropyl 2-oxo-4-phenyl-2H-pyrimido[2,1-b]benzothiazole-8-acetate was obtained.

EXAMPLE 7 n-Butyl 2-oxo-4-phenyl-2H-pyrimido[2,1-b]benzothiazole-8-acetate

Using the procedure of Example 3 with corresponding compound of formula II wherein $R_1'$ is n-butoxy and ethyl phenylpropiolate (compound of formula III), n-butyl 2-oxo-4-phenyl-2H-pyrimido[2,1-b]benzothiazole-8-acetate was obtained.

EXAMPLE 8

2-oxo-4-phenyl-2H-pyrimido[2,1-b]benzothiazole-8-acetic acid

A stirred mixture of 2.47 g of ethyl-2-oxo-4-phenyl-2H-pyrimido[2,1-b]benzothiazole-8-acetate, 100 ml of methanol and a solution of 2.47 g of potassium carbonate in 20 ml of water was kept at ambient temperature overnight. The methanol was evaporated and the residue was diluted with water, then acidified with concentrated hydrochloric acid. The precipitate was collected, dried, and crystallized twice from methanol to obtain 1.72 g (75% yield) of 2-oxo-4-phenyl-2H-pyrimido[2,1-b]benzothiazole-8-acetic acid as yellow plates.

EXAMPLES 9 TO 19

Using the procedure of Example 3, ethyl 2-aminobenzothiazole-6-acetate of formula II and the compounds of formula III in which $R_2$ has the meanings indicated in Table I below and $R_4$ is ethyl, the following compounds were prepared:

Example 9: Ethyl 4-(4-methoxyphenyl)-2-oxo-2H-pyrimido[2,1-b]benzothiazole-8-acetate.
Example 10: Ethyl 4-(4-nitrophenyl)-2-oxo-2H-pyrimido[2,1-b]benzothiazole-8-acetate.
Example 11: Ethyl 4-(4-chlorophenyl)-2-oxo-2H-pyrimido[2,1-b]benzothiazole-8-acetate.
Example 12: Ethyl 4-(2-chlorophenyl)-2-oxo-2H-pyrimido[2,1-b]benzothiazole-8-acetate.
Example 13: Ethyl 4-(4-methylphenyl)-2-oxo-2H-pyrimido[2,1-b]benzothiazole-8-acetate.
Example 14: Ethyl 4-(3-chlorophenyl)-2-oxo-2H-pyrimido[2,1-b]benzothiazole-8-acetate.
Example 15: Ethyl 4-methyl-2-oxo-2H-pyrimido[2,1-b]benzothiazole-8-acetate.
Example 16: Ethyl 4-ethyl-2-oxo-2H-pyrimido[2,1-b]benzothiazole-8-acetate.
Example 17: Ethyl 2-oxo-4-n-propyl-2H-pyrimido[2,1-b]benzothiazole-8-acetate.
Example 18: Ethyl 4-n-butyl-2-oxo-2H-pyrimido[2,1-b]benzothiazole-8-acetate.
Example 19: Ethyl 4-methoxycarbonyl-2-oxo-2H-pyrimido[2,1-b]benzothiazole-8-acetate.

EXAMPLE 20

Ethyl α-methyl-2-oxo-4-phenyl-2H-pyrimido[2,1-b]benzothiazole-8-acetate

A mixture of 50 g of ethyl 2-amino-α-methylbenzothiazole-6-acetate and 34.9 g of ethyl phenylpropiolate was heated with stirring in an oil bath at 100° C. for 20 hours, after which time a further 7 g of ethyl phenylpropiolate were added. Heating was continued for a further 96 hours and HPLC showed the reaction to be 93% complete. 500 ml of ether were then added cautiously and the mixture was stirred at reflux for 2 hours. Seeds of ethyl α-methyl-2-oxo-4-phenyl-2H-pyrimido[2,1-b]benzothiazole-8-acetate were added and the solution was cooled. The crystalline product was filtered off and washed with ether, then dried to obtain 39 g (51% yield) of ethyl α-methyl-2-oxo-4-phenyl-2H-pyrimido[2,1-b]benzothiazole-8-acetate (99.9% pure HPLC) melting at 127°–31° C.

EXAMPLE 21

α-Methyl-2-oxo-4-phenyl-2H-pyrimido[2,1-b]benzothiazole-8-acetic acid

Using the procedure of example 8 with ethyl α-methyl 2-oxo 4-phenyl 2H-pyrimido[2,1-b]benzothiazole obtained according to example 20, α-methyl-2-oxo-4-phenyl-2H-pyrimido[2,1-b]benzothiazole 8-acetic acid was prepared.

Using the procedure of Example 20, ethyl 2-amino-α-methyl benzothiazole-6-acetate and the compounds of formula III wherein $R_2$ has the meanings indicated in Table I below and $R_4$ is ethyl the following compounds were prepared.

Example 22: Ethyl α-methyl 4-(4-chlorophenyl)-2-oxo-2H-pyrimido[2,1-b]benzothiazole-8-acetate.
Example 23: Ethyl α-methyl 4-(3-chlorophenyl) 2-oxo-2H-pyrimido[2,1-b]benzothiazole-8-acetate.
Example 24: Ethyl α-methyl-2-oxo-4-n-propyl-2H-pyrimido[2,1-b]benzothiazole-8-acetate.

EXAMPLE 25 TO 43:

Using the procedure described above and starting from appropriate compounds of formulae II and III, the following compounds were prepared:

Example 25: Ethyl 4-isopropyl-2-oxo-2H-pyrimido[2,1-b]benzothiazole-8-acetate.
Example 26: Ethyl 4-benzyl-2-oxo-2H-pyrimido[2,1-b]benzothiazole-8-acetate.

Example 27: Ethyl α-methyl-4-benzyl-2-oxo-2H-pyrimido[2,1-b]benzothiazole-8-acetate.
Example 28: Ethyl α-methyl-4-isopropyl-2-oxo-2H-pyrimido[2,1-b]benzothiazole-8-acetate.
Example 29: Ethyl α-ethyl-4-phenyl-2-oxo-2H-pyrimido[2,1-b]benzothiazole-8-acetate.
Example 30: Ethyl 4-cyclohexyl-2-oxo-2H-pyrimido[2,1-b]benzothiazole-8-acetate.
Example 31: Ethyl α-methyl-4-cyclohexyl-2-oxo-2H-pyrimido[2,1-b]benzothiazole-8-acetate.
Example 32: Ethyl α-propyl-4-phenyl-2-oxo-2H-pyrimido[2,1-b]benzothiazole-8-acetate.
Example 33: Ethyl α-isopropyl-4-phenyl-2-oxo-2H-pyrimido[2,1-b]benzothiazole-8-acetate.
Example 34: Ethyl α-butyl-4-phenyl-2-oxo-2H-pyrimido[2,1-b]benzothiazole-8-acetate.
Example 35: Isopropyl α-methyl-4-phenyl-2-oxo-2H-pyrimido[2,1-b]benzothiazole-8-acetate.
Example 36: Ethyl α,α-dimethyl-4-phenyl-2-oxo-2H-pyrimido[2,1-b]benzothiazole-8-acetate.
Example 37: Ethyl α-ethyl-α-methyl-4-phenyl-2-oxo-2H-pyrimido[2,1-b]benzothiazole-8-acetate.
Example 38: Ethyl α-methyl-α-propyl-4-phenyl-2-oxo-2H-pyrimido[2,1-b]benzothiazole-8-acetate.
Example 39: t-Butyl α-methyl-4-phenyl-2-oxo-2H-pyrimido[2,1-b]benzothiazole-8-acetate.
Example 40: Ethyl α,α-diethyl-4-phenyl-2-oxo-2H-pyrimido[2,1-b]benzothiazole-8-acetate.
Example 41: Ethyl α-ethyl-α-propyl-4-phenyl-2-oxo-2H-pyrimido[2,1-b]benzothiazole-8-acetate.
Example 42: Ethyl α-butyl-α-methyl-4-phenyl-2-oxo-2H-pyrimido[2,1-b]benzothiazole-8-acetate.
Example 43: 2,2-Dimethylpropyl α-methyl-4-phenyl-2-oxo-2H-pyrimido[2,1-b]benzothiazole-8-acetate.

EXAMPLE 44

N,N-dimethyl-2-oxo-4-phenyl-2H-pyrimido[2,1-b]benzothiazole-8-acetamide

A solution of 3 g of 2-oxo-4-phenyl-2H-pyrimido[2,1-b]benzothiazole-8-acetic acid in 40 ml of tetrahydrofuran and 2 g of 1,1'-carbonyldiimidazole were admixed. The mixture was stirred at room temperature for 1 hour until dissolution took place. Excess dimethylamine (30% in ethanol) was added and the mixture was stirred for a further 40 minutes. The solvent was then removed under vacuo and the residue was taken up in dichloromethane and washed with water, bicarbonate solution water then dried over $MgSO_4$, filtered and evaporated to dryness to obtain 1.1 g of N,N-dimethyl-2-oxo-4-phenyl-2H-pyrimido[2,1-b]benzothiazole-8-acetamide as a pale buff solid which was purified by flash chromatography on silica. It had a melting point of 238°–40° C.

EXAMPLES 45 TO 48

Using the methods described above but using the appropriate amine starting material, the following compounds were prepared:
Example 45: N-ethyl-2-oxo-4-phenyl-2H-pyrimido[2,1-b]benzothiazole-8-acetamide.
Example 46: 1-(N-morpholino)-2-(2-oxo-4-phenyl-2H-pyrimido[2,1-b]benzothiazole-8-yl)-ethanone.
Example 47: N,N-diethyl-2-oxo-4-phenyl-2H-pyrimido[2,1-b]benzothiazole-8-acetamide.
Example 48: 1-(N-piperidino)-2-(2-oxo-4-phenyl-2H-pyrimido[2,1-b]benzothiazole-8-yl)-ethanone.

TABLE 1

| Example | R | $R_1$ | $R_2$ | $R_3$ | M. pt. °C. |
|---|---|---|---|---|---|
| 1 | H | EtO | H | H | 276 |
| 2 | Me | EtO | H | H | 129 |
| 3 | H | EtO | Ph | H | 206 |
| 4 | H | MeO | Ph | H | 225–6 |
| 5 | H | nPrO | Ph | H | 133.5–134.5 |
| 6 | H | isoPrO | Ph | H | 171.5–172.5 |
| 7 | H | nBuO | Ph | H | 136–7 |
| 8 | H | HO | Ph | H | slight decompos. 136° C. m. 256° C. |
| 9 | H | EtO | p-MeOPh | H | 152 |
| 10 | H | EtO | p-$NO_2$Ph | H | 246 |
| 11 | H | EtO | p-ClPh | H | 220 |
| 12 | H | EtO | o-ClPh | H | 196.5 |
| 13 | H | EtO | p-MePh | H | 183–4 |
| 14 | H | EtO | m-ClPh | H | 176–9 |
| 15 | H | EtO | Me | H | 251–3 |
| 16 | H | EtO | Et | H | 166.7 |
| 17 | H | EtO | nPr | H | 158–60 |
| 18 | H | EtO | nBu | H | 149.6 |
| 19 | H | EtO | $CO_2$Me | H | 163 |
| 20 | Me | EtO | Ph | H | 127–31 |
| 21 | Me | HO | Ph | H | 239–46 |
| 22 | Me | EtO | p-ClPh | H | 190–1 |
| 23 | Me | EtO | m-ClPh | H | 76–9 |
| 24 | Me | EtO | nPr | H | 125–6 |
| 25 | H | EtO | isoPr | H | 170–2 |
| 26 | H | EtO | $CH_2$Ph | H | 197–9 |
| 27 | Me | EtO | $CH_2$Ph | H | 99–101 |
| 28 | Me | EtO | isoPr | H | 149–51 |
| 29 | Et | EtO | Ph | H | 143–5 |
| 30 | H | EtO | cyclohexyl | H | 169–71 |
| 31 | Me | EtO | cylcohexyl | H | 148–50 |
| 32 | nPr | EtO | Ph | H | 131–3 |
| 33 | isoPr | EtO | Ph | H | 126–8 |
| 34 | Bu | EtO | Ph | H | 92–94 |
| 35 | Me | isoPrO | Ph | H | 153–5 |
| 36 | Me | EtO | Ph | Me | 133–5 |
| 37 | Me | EtO | Ph | Et | 159–61 |
| 38 | Me | EtO | Ph | Pr | 174–6 |
| 39 | Me | t-BuO | Ph | H | 122–5 |
| 40 | Et | EtO | Ph | Et | 138–40 |
| 41 | Et | EtO | Ph | Pr | 163–4 |
| 42 | Me | EtO | Ph | Bu | 143–4 |
| 43 | Me | t-BuC$H_2$O | Ph | H | 122–3 |
| 44 | H | $Me_2$N | Ph | H | 238–40 |
| 45 | H | EtHN | Ph | H | 210–2 |
| 46 | H | O〈_N | Ph | H | 214–6 |
| 47 | H | $Et_2$N | Ph | H | 147–9 |
| 48 | H | 〈_N | Ph | H | 190–1 |

| Example | Formula | CALCULATED* % C | % H | N % | S % |
|---|---|---|---|---|---|
| 1 | $C_{14}H_{12}N_2O_3S$ | 58.3 | 4.2 | 9.7 | 11.1 |
| 2 | $C_{15}H_{14}N_2O_3S$ | 59.6 | 4.65 | 9.25 | 10.6 |
| 3 | $C_{20}H_{16}N_2O_3S$ | 65.9 | 4.4 | 7.7 | 8.8 |
| 4 | — | — | — | — | — |
| 5 | $C_{21}H_{18}N_2O_3S$ | 66.65 | 4.8 | 7.4 | 8.45 |
| 6 | $C_{21}H_{18}N_2O_3S$ | 66.65 | 4.8 | 7.4 | 8.45 |
| 7 | $C_{22}H_{19}N_2O_3S$ | 67.35 | 5.15 | 7.15 | 8.15 |
| 8 | $C_{18}H_{12}N_2O_3S$ | 64.25 | 3.6 | 8.35 | 9.55 |
| 9 | $C_{21}H_{18}N_2O_4S$ | 63.95 | 4.6 | 7.1 | 8.15 |
| 10 | $C_{20}H_{15}N_3O_5S$ | 58.65 | 3.7 | 10.25 | 7.85 |
| 11 | $C_{20}H_{15}N_2O_3ClS$ | 60.2 | 3.8 | 7.0 | 8.05 |
| 12 | $C_{20}H_{15}N_2O_3ClS$ | 60.2 | 3.8 | 7.0 | 8.05 |
| 13 | $C_{21}H_{18}N_2O_3S$ | 66.65 | 4.8 | 7.4 | 8.45 |

TABLE 1-continued

| Example | Formula | | | | |
|---|---|---|---|---|---|
| 14 | $C_{20}H_{15}N_2O_3ClS$ | 60.2 | 3.8 | 7.0 | 8.05 |
| 15 | $C_{15}H_{14}N_2O_3S$ | 59.6 | 4.65 | 9.25 | 10.6 |
| 16 | $C_{16}H_{16}N_2O_3S$ | 60.75 | 5.1 | 8.85 | 10.15 |
| 17 | $C_{17}H_{18}N_2O_3S$ | 61.8 | 5.5 | 8.5 | 9.7 |
| 18 | $C_{18}H_{20}N_2O_3S$ | 62.75 | 5.85 | 8.15 | 9.3 |
| 19 | $C_{16}H_{14}N_2O_5S$ | 55.5 | 4.05 | 8.1 | 9.25 |
| 20 | $C_{21}H_{18}N_2O_3S$ | 66.65 | 4.8 | 7.4 | 8.45 |
| 21 | $C_{19}H_{14}N_2O_3S$ | 66.15 | 4.05 | 8.0 | 9.15 |
| 22 | $C_{21}H_{17}N_2O_3ClS$ | 61.1 | 4.15 | 6.8 | 7.75 |
| 23 | $C_{21}H_{17}N_2O_3ClS$ | 61.1 | 4.15 | 6.8 | 7.75 |
| 24 | $C_{18}H_{20}N_2O_3S$ | 62.75 | 5.85 | 8.15 | 9.3 |
| 25 | $C_{17}H_{18}N_2O_3S$ | 61.80 | 5.49 | 8.48 | 9.70 |
| 26 | $C_{21}H_{18}N_2O_3S$ | 66.65 | 4.79 | 7.40 | 8.47 |
| 27 | $C_{22}H_{20}N_2O_3S \cdot \frac{1}{2}H_2O$ | 65.82 | 5.27 | 6.98 | 7.99 |
| 28 | $C_{18}H_{20}N_2O_3S$ | 62.77 | 5.85 | 8.13 | 9.29 |
| 29 | $C_{22}H_{20}N_2O_3S$ | 67.33 | 5.14 | 7.14 | 8.17 |
| 30 | $C_{20}H_{22}N_2O_3S$ | 64.84 | 5.99 | 7.56 | 8.65 |
| 31 | $C_{21}H_{24}N_2O_3S$ | 65.60 | 6.29 | 7.28 | 8.34 |
| 32 | $C_{23}H_{22}N_2O_3S$ | 67.96 | 5.46 | 6.89 | 7.89 |
| 33 | $C_{23}H_{22}N_2O_3S \cdot \frac{1}{2}H_2O$ | 66.49 | 5.58 | 6.74 | 7.72 |
| 34 | $C_{24}H_{24}N_2O_3S$ | 68.55 | 5.75 | 6.66 | 7.62 |
| 35 | $C_{22}H_{20}N_2O_3S$ | 67.33 | 5.14 | 7.14 | 8.17 |
| 36 | $C_{22}H_{20}N_2O_3S$ | 67.33 | 5.14 | 7.14 | 8.17 |
| 37 | $C_{23}H_{22}N_2O_3S$ | 67.96 | 5.46 | 6.89 | 7.89 |
| 38 | $C_{24}H_{24}N_2O_3S$ | 68.55 | 5.75 | 6.66 | 7.62 |
| 39 | $C_{23}H_{22}N_2O_3S$ | 67.96 | 5.46 | 6.89 | 7.89 |
| 40 | $C_{24}H_{24}N_2O_3S$ | 68.55 | 5.75 | 6.66 | 7.62 |
| 41 | $C_{25}H_{26}N_2O_3S$ | 69.10 | 6.03 | 6.45 | 7.38 |
| 42 | $C_{25}H_{26}N_2O_3S$ | 69.10 | 6.03 | 6.45 | 7.38 |
| 43 | $C_{24}H_{24}N_2O_3S$ | 68.55 | 5.75 | 6.66 | 7.62 |
| 44 | $C_{20}H_{17}N_3O_2S \cdot \frac{1}{2}H_2O$ | 64.50 | 4.87 | 11.28 | 8.61 |
| 45 | $C_{20}H_{17}N_3O_2S \cdot \frac{1}{2}H_2O$ | 64.50 | 4.87 | 11.28 | 8.61 |
| 46 | $C_{22}H_{19}N_3O_2S \cdot \frac{1}{2}H_2O$ | 63.75 | 4.86 | 10.14 | 7.73 |
| 47 | $C_{22}H_{21}N_3O_2S$ | 67.50 | 5.41 | 10.73 | 8.19 |
| 48 | $C_{23}H_{21}N_3O_2S$ | 68.45 | 5.25 | 10.41 | 7.95 |

| Example | FOUND* | | | |
|---|---|---|---|---|
| | % C | % H | % N | % S |
| 1 | 58.25 | 4.25 | 9.75 | 11.1 |
| 2 | 59.5 | 4.65 | 9.3 | 10.45 |
| 3 | 66.2 | 4.5 | 7.65 | 8.85 |
| 4 | — | — | — | — |
| 5 | 66.55 | 4.85 | 7.35 | 8.35 |
| 6 | 66.65 | 4.85 | 7.4 | 8.45 |
| 7 | 67.35 | 5.15 | 7.2 | 8.2 |
| 8 | 64.25 | 3.65 | 8.3 | 9.55 |
| 9 | 64.05 | 4.65 | 7.1 | 8.2 |
| 10 | 58.6 | 3.75 | 10.25 | 7.8 |
| 11 | 60.15 | 3.85 | 6.95 | 8.05 |
| 12 | 60.25 | 3.9 | 7.0 | 8.1 |
| 13 | 66.45 | 4.85 | 7.40 | 8.6 |
| 14 | 60.25 | 3.9 | 7.05 | 8.1 |
| 15 | 59.6 | 4.7 | 9.3 | 10.55 |
| 16 | 60.5 | 5.1 | 8.8 | 10.15 |
| 17 | 61.7 | 5.5 | 8.45 | 9.75 |
| 18 | 62.5 | 5.9 | 8.15 | 9.45 |
| 19 | 55.3 | 4.15 | 8.0 | 9.15 |
| 20 | 66.5 | 4.85 | 7.45 | 8.4 |
| 21 | 64.9 | 4.05 | 8.0 | 9.1 |
| 22 | 61.1 | 4.25 | 6.75 | 7.75 |
| 23 | 60.85 | 4.3 | 6.75 | 7.85 |
| 24 | 62.65 | 5.85 | 8.15 | 9.3 |
| 25 | 61.88 | 5.51 | 8.51 | 9.64 |
| 26 | 66.55 | 4.85 | 7.37 | 8.43 |
| 27 | 65.94 | 5.34 | 6.88 | 8.02 |
| 28 | 62.73 | 5.93 | 8.11 | 9.17 |
| 29 | 67.43 | 5.16 | 7.14 | 8.12 |
| 30 | 64.85 | 5.95 | 7.62 | 8.64 |
| 31 | 65.62 | 6.34 | 7.21 | 8.35 |
| 32 | 67.84 | 5.54 | 6.85 | 7.75 |
| 33 | 66.56 | 5.59 | 6.61 | 7.65 |
| 34 | 68.35 | 5.83 | 6.62 | 7.72 |
| 35 | 67.27 | 5.20 | 7.08 | 7.97 |
| 36 | 67.42 | 5.16 | 7.09 | 8.22 |
| 37 | 67.66 | 5.66 | 6.67 | 7.59 |
| 38 | 68.30 | 5.86 | 6.54 | 7.53 |
| 39 | 68.10 | 5.50 | 6.84 | 7.87 |
| 40 | 68.47 | 5.85 | 6.58 | 7.61 |
| 41 | 69.08 | 6.14 | 6.34 | 7.37 |
| 42 | 68.91 | 6.14 | 6.32 | 7.28 |
| 43 | 68.62 | 5.78 | 6.66 | 7.63 |
| 44 | 64.50 | 4.72 | 11.18 | 8.54 |
| 45 | 64.46 | 4.71 | 11.28 | 8.62 |
| 46 | 63.86 | 4.76 | 10.00 | 7.75 |
| 47 | 67.20 | 5.40 | 10.58 | 8.17 |
| 48 | 68.19 | 5.31 | 10.26 | 7.95 |

*ANALYSES (to nearest 0.05%)

EXAMPLE 49

1-Methylcyclohexyl
α-methyl-2-oxo-4-phenyl-2H-pyrimido[2,1-b]benzo-thiazole-8-acetate

STEP A: 1-Methylcyclohexyl 2-(p-nitrophenyl)-propionate

A stirred mixture of 97.5 g of 2-(p-nitrophenyl)-propionic acid [J. Med. Chem. Vol. 26, pages 222–226 (1983)], 40 ml of thionyl chloride and 500 ml of dry toluene was heated at 80° C. for 5 hours. The mixture was then allowed to cool and the solvent was evaporated under reduced pressure. The residual oil was dissolved in 400 ml of dry toluene, and 100 g of 1-methylcyclohexanol were added to the solution. The stirred mixture was heated at 80° C. for 1 hour and then at ambient temperature overnight. The solution was washed with 5% NaHCO₃ solution, then water, dried over MgSO₄ and finally evaporated to dryness. The crude mixture was purified over a column of 600 g of silica using CHCl₃ as the eluant 34.95 g (24% yield) of 1-methyl-cyclohexyl 2-(p-nitrophenyl)-propionate as a golden yellow liquid.

IR $\nu_{max}$ (thin film): 2940, 1725 (ester), 1520, 1345 and 1150 cm$^{-1}$

STEP B: 1-Methylcyclohexyl 2-(p-aminophenyl)-propionate

A stirred solution of 34.9 g of 1-methylcyclohexyl 2-(p-nitrophenyl)-propionate in 250 ml of absolute ethanol was hydrogenated at atmospheric pressure in the presence of 10% palladium on carbon catalyst. After the uptake of hydrogen gas was complete, the catalyst was filtered off through celite and the filtrate was evaporated to dryness. Trituration of the residue with petroleum ether gave 21.02 g (67% yield) of 1-methylcyclohexyl 2-(p-aminophenyl)-propionate as creamy white crystals melting at 85°–87° C.

IR$_{max}$ (KBr): 3640 (—NH₂), 3370 (—NH₂), 2940, 1710 and 1215 cm$^{-1}$.

STEP C: 1-Methylcyclohexyl 2-amino-α-methylbenzothiazole-6-acetate

A stirred mixture of 20.9 g of 1-methylcyclohexyl 2-(p-aminophenyl)-propionate and 31.0 g of potassium thiocyanate in 150 ml of glacial acetic acid was heated in an oil bath at 50° C. and a solution of 25.6 g of Br₂ in 15 ml of glacial acetic acid was added dropwise over 30 minutes. The mixture was stirred at 50° C. for an extra 30 minutes, then was cooled and poured into 1,000 ml of 3:2 water/ethyl acetate mixture. The resulting mixture was neutralized to pH 5–6 with solid Na₂CO₃ and filtered through celite, and the organic layer was then separated, washed with water, dried over MgSO₄ and finally evaporated to dryness. Trituration of the residual oil with petroleum ether gave 18.62 g (73% yield) of 1-methylcyclohexyl 2-amino-α-methylbenzothiazole-6-acetate as creamy white crystals melting at 165°–167° C.

IR $\nu_{max}$ (KBr): 3410, 2930, 1710 (ester), 1550 and 1215 cm$^{-1}$.

STEP D: 1-Methylcyclohexyl α-methyl-2-oxo-4-phenyl-2H-pyrimido[2,1-b]benzothiazole-8-acetate A stirred mixture of 3.2 g of 1-methylcyclohexyl 2-amino-α-methylbenzothiazole-6-acetate and 3.5 g of ethyl phenyl-propionate was heated in an oil bath at 160° C. for 30 minutes during which time a further 3.5 g of ethyl phenylpropionate were added dropwise. The mixture was then cooled to 60° C. and 30 ml of ether were cautiously added. Further cooling gave 1.82 g (41% yield) of 1-methylcyclohexyl α-methyl-2-oxo-4-phenyl-2H-pyrimido[2,1b]benzothiazole-8-acetate as pale yellow crystals melting at 168°–170° C.

IR $\nu_{max}$ (KBr): 2930, 1720 (ester), 1650, 1510 and 1145 cm$^{-1}$.

Analysis: Calculated: %C 69.93; %H 5.87; %N 6.27; %S 7.18; Found: C 69.87; H 5.90; N 6.23; S 7.23

EXAMPLE 50

1-Adamantyl α-methyl-2-oxo-4-phenyl-2H-pyrimido[2,1-b]benzothiazole-8-acetate

STEP A: 1-Adamantyl 2-(p-nitrophenyl)propionate

Using a method similar to that used in the preparation of 1-methylcyclohexyl 2-(p-nitrophenyl)propionate, 14.6 g of 2-(p-nitrophenyl)propionic acid, but using 1-adamantol instead of 1-methylcyclohexanol, were reacted to obtain 22.74 g (92% yield) of 1-adamantyl 2-(p-nitrophenyl)propionate as a light yellow viscous liquid.

IR $\nu_{max}$ (thin film): 2920, 1725 (ester, 1520, 1345 and 1055 cm$^{-1}$.

STEP B: 1-Adamantyl 2-(p-aminophenyl)propionate

Using a method similar to that used in the preparation of 1-methylcyclohexyl 2-(p-aminophenyl)-propionate, 21.4 g of 1-adamantyl 2-(p-nitrophenyl)propionate were reacted to obtain 19.42 g (100% yield) of 1-adamantyl 2-(p-aminophenyl)propionate of a light yellow viscous liquid.

IR $\nu_{max}$ (thin film): 3450 (—NH$_2$), 3370 (—NH$_2$), 2910, 1720 (ester) and 1055 cm$^{-1}$ STEP C: 1-Adamantyl 2-amino-α-methylbenzothiazole-6-acetate Using the methpod similar to that used in the preparation of 1-methylcyclohexyl 2-amino-α-methylbenzothiazole-6-acetate, 19.1 g of 1-adamantyl 2-(p-aminophenyl)propionate were reacted to obtain 18.97 g (83% yield) of 1-adamantyl 2-amino-α-methylbenzothiazole-6-acetate as a creamy white solid melting at 151°–153° C.

IR $\nu_{max}$ (KBr): 3400, 2910, 1710 (ester), 1540 and 1210 cm$^{-1}$.

STEP D: 1-Adamantyl α-methyl-2-oxo-4-phenyl-2H-pyrimido[2,1-b]benzothiazole-8-acetate Using a method similar to that used in the preparation of 1-methylcyclohexyl α-methyl-2-oxo-4-phenyl-2H-pyrimido[2,1-b]benzothiazole-8-acetate, 8.9 g of 1-adamantyl 2-amino-α-methylbenzothiazole-6-acetate were reacted with heating at 160° C. for 1 hour to obtain 4.73 g (39% yield) of 1-adamantyl α-methyl-2-oxo-4-phenyl-2H-pyrimido[2,1-b]benzothiazole-8-acetate as a yellow solid after crystallization from ethyl acetate/petroleum ether melting at 188°–190° C.

IR $\nu_{max}$ (KBr): 2910, 1720 (ester), 1640, 1510 and 1390 cm$^{-1}$.

Calculated: %C 71.88; %H 5.82; %N 5.78; %S 6.62; Found: %C 71.71; %H 5.87; %N 5.75; %S 6.57.

EXAMPLE 51

Tablets were prepared containing 15 mg of either the compound of Example 3 or 49 or 50 or of Example 20 and sufficient excipient of lactose, starch, talc and magnesium stearate q.s. for a final weight of 100 mg.

EXAMPLE 52

A dosed aerosol was prepared delivering per dose: 2 mg of the compound of Example 20 or Example 50, 0.15 mg of an emulsifier and 50 mg of propellant.

PHARMACOLOGICAL DATA

Antigen-induced elevation of lung perfusion pressure

Male Dunkin Hartley guinea pigs (Porcellus) weighing between 450–700 g were used (four per test concentration) and were housed in cages. The animals were sensitized by two weekly exposures to 1% W/V aerosol ovalbumen. The animals were anaesthetized with 2.5 mg/kg diazepam i.p. and 1 ml/kg Hyponorm i.m. Following anaethesia, the animals were exsanguinated by severing both carotid arteries and the chest was opened and the lungs removed, split into two at the carina and both cannulated via the main lobar bronchus and connected to a perfusion system. The lungs were perfused with aerated krebs fluid (95% O$_2$:5% CO$_2$) at 37° C. and 5 µg in 0.1 ml Ovalbumen was injected through an injection port proximal to each lung. Elevation of perfusion pressure by the antigen was recorded and sixty minutes later, 15 µg of ovalbumen were administered. The test compounds were added to the krebs fluid reservoir thirty minutes prior to the second antigen dose. For each weekly batch of animals used, control measurements were made without treatment (n=10). The second antigen response was expressed as a percentage of the first. For each test, at least four lungs from four different animals were used per concentration. The percentage inhibition of antigen induced broncho-constriction was calculated. (IC$_{50}$uM) and the results are given in Table below.

TABLE 2

| Product of Example | IC$_{50}$ uM |
|---|---|
| 2 | >100 |
| 3 | 1 |
| 4 | 10 |
| 5 | <10 |
| 6 | 1–10 |
| 7 | >10 |
| 9 | 1 |
| 10 | 10–100 |
| 11 | 10 |
| 12 | 0.1–1 |
| 13 | <1 |
| 14 | ≦1 |
| 15 | 10–100 |
| 16 | 100 |
| 17 | 1–10 |
| 18 | 10 |
| 20 | 0.1 |
| 22 | 0.1–1 |
| 23 | ≦1 |
| 24 | >10 |
| 25 | 10–100 |
| 27 | 10–100 |

TABLE 2-continued

| Product of Example | IC$_{50}$ uM |
|---|---|
| 28 | 10–100 |
| 29 | 0.1 |
| 30 | 1–10 |
| 31 | <10 |
| 32 | 1 |
| 33 | 10–100 |
| 34 | 1–10 |
| 35 | 0.1–1 |
| 36 | 1–10 |
| 37 | 1 |
| 38 | 1 |
| 39 | 0.1 |
| 40 | 10–100 |
| 41 | 10–100 |
| 42 | 10–100 |
| 43 | 0.1 |
| 44 | 10–100 |
| 45 | 10–100 |
| 46 | >100 |
| 47 | 10 |
| 48 | 10–100 |
| 49 | 1 to 10 |
| 50 | ≦1 |

Various modifications of the compounds and method of the invention may be made without departing from the spirit or scope thereof and it is to be understood that the invention is intended to be limited only as defined in the appended claims.

What is claimed is:

1. A compound selected from the group consisting of pyrimido[2,1-b]benzothiazoles of the formula

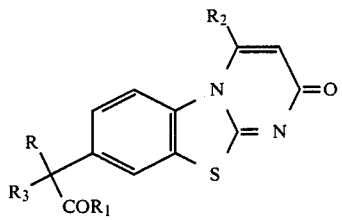

wherein R and R$_3$ are individually selected from the group consisting of hydrogen and alkyl of 1 to 6 carbon atoms or taken together with the carbon to which they are attached form a cycloalkyl of 3 to 6 carbon atoms, R$_1$ is selected from the group consisting of hydroxy, alkoxy of 1 to 12 carbon atoms, cycloalkoxy of 7 to 12 carbon atoms and

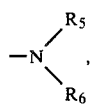

R$_5$ and R$_6$ are individually selected from the group consisting of hydrogen and alkyl of 1 to 6 carbon atoms or taken together with the nitrogen form piperidino or morpholino, R$_2$ is selected from the group consisting of hydrogen, alkyl of 1 to 6 carbon atoms, alkoxycarbonyl of 2 to 7 carbon atoms, cycloalkyl of 3 to 6 carbon atoms, 2-thienyl, phenylalkyl and optionally substituted phenyl with at least one substituent selected from the group consisting of halogen, nitro and alkyl and alkoxy of 1 to 6 carbon atoms and their salts with non-toxic, pharmaceutically acceptable acids and bases.

2. A compound of claim 1 wherein R and R$_3$ are individually selected from the group consisting of hydrogen, methyl and ethyl.

3. A compound of claim 2 wherein R$_2$ is selected from the group consisting of hydrogen, alkyl of 1 to 6 carbon atoms, methoxycarbonyl and phenyl optionally substituted with at least one member of the group consisting of halogen, nitro, methyl and methoxy.

4. A compound of claim 2 wherein R$_2$ is phenyl and R$_1$ is 1-methylcyclohexyloxy or 1-adamantyloxy.

5. A compound of claim 1 selected from the group consisting of ethyl 2-oxo-4-phenyl-2H-pyrimido[2,1-b]benzothiazole-8-acetate and its non-toxic, pharmaceutically acceptable salts.

6. A compound of claim 1 selected from the group consisting of ethyl 2-oxo-4-(p-methoxyphenyl)-2H-pyrimido[2,1-b]benzothiazole-8-acetate and its non-toxic, pharmaceutically acceptable salts.

7. A compound of claim 1 selected from the group consisting of ethyl 2-oxo-4-(o-chlorophenyl)-2H-pyrimido[2,1-b]benzothiazole-8-acetate and its non-toxic, pharmaceutically acceptable salts.

8. A compound of claim 1 selected from the group consisting of ethyl α-methyl-2-oxo-4-phenyl-2H-pyrimido[2,1-b]benzothiazole-8-acetate and its non-toxic, pharmaceutically acceptable salts.

9. A compound of claim 1 selected from the group consisting of ethyl α-methyl-2-oxo-4-(p-chlorophenyl)-2H-pyrimido[2,1-b]benzothiazole-8-acetate and its non-toxic, pharmaceutically acceptable salts.

10. A compound of claim 1 selected from the group consisting of ethyl α-ethyl-2-oxo-4-phenyl-2H-pyrimido[2,1-b]benzothiazole-8-acetate and its non-toxic, pharmaceutically acceptable salts.

11. A compound of claim 1 selected from the group consisting of 1-methylcyclohexyl α-methyl-2-oxo-4-phenyl-2H-pyrimido[2,1-b]benzothiazole-8-acetate and its non-toxic, pharmaceutically acceptable salts.

12. A compound of claim 1 selected from the group consisting of 1-adamantyl α-methyl-2-oxo-4-phenyl-2H-pyrimido[2,1-b]benzothiazole-8-acetate and its non-toxic, pharmaceutically acceptable salts.

13. An antiallergic composition comprising an antiallergically effective amount of at least one compound of claim 1 and an excipient.

14. A composition of claim 13 wherein in the compound R and R$_3$ are individually selected from the group consisting of hydrogen, methyl and ethyl.

15. A composition of claim 13 wherein in the compound R$_2$ is selected from the group consisting of hydrogen, alkyl of 1 to 6 carbon atoms, methoxycarbonyl and phenyl optionally substituted with at least one member of the group consisting of halogen, nitro, methyl and methoxy.

16. A composition of claim 13 wherein the compound is selected from the group consisting of ethyl 2-oxo-4-phenyl-2H-pyrimido[2,1-b]benzothiazole-8-acetate and its non-toxic, pharmaceutically acceptable salts.

17. A composition of claim 13 wherein the compound is selected from the group consisting of ethyl 2-oxo-4-(p-methoxyphenyl)-2H-pyrimido[2,1-b]benzothiazole-8-acetate and its non-toxic, pharmaceutically acceptable salts.

18. A composition of claim 13 wherein the compound is selected from the group consisting of ethyl 2-oxo-4-(o-chlorophenyl)-2H-pyrimido[2,1-b]benzothiazole-8-acetate and its non-toxic, pharmaceutically acceptable salts.

19. A composition of claim 13 wherein the compound is selected from the group consisting of ethyl α-methyl-2-oxo-4-phenyl-2H-pyrimido[2,1-b]benzothiazole-8-acetate and its non-toxic, pharmaceutically acceptable salts.

20. A composition of claim 13 wherein the compound is selected from the group consisting of ethyl α-methyl-2-oxo-4-(p-chlorophenyl)-2H-pyrimido[2,1-b]benzothiazole-8-acetate and its non-toxic, pharmaceutically acceptable salts.

21. A composition of claim 13 wherein the compound is selected from the group consisting of ethyl α-ethyl-2-oxo-4-phenyl-2H-pyrimido[2,1-b]benzothiazole-8-acetate and its non-toxic, pharmaceutically acceptable salts.

22. A composition of claim 13 wherein the compound is selected from the group consisting of 1-methylcyclohexyl α-methyl-2-oxo-4-phenyl-2H-pyrimido[2,1-b]benzothiazole-8-acetate and its non-toxic, pharmaceutically acceptable salts.

23. A composition of claim 13 wherein the compound is selected from the group consisting of 1-adamantyl α-methyl-2-oxo-4-phenyl-2H-pyrimido[2,1-b]benzothiazole-8-acetate and its non-toxic, pharmaceutically acceptable salts.

24. A method of treating allergies in warm-blooded animals comprising administering to warm-blooded animals an antiallergically effective amount of at least one compound of claim 1.

25. A method of claim 24 wherein in the compound R and $R_3$ are individually selected from the group consisting of hydrogen, methyl and ethyl.

26. A method of claim 24 wherein in the compound $R_2$ is selected from the group consisting of hydrogen, alkyl of 1 to 6 carbon atoms, methoxycarbonyl and phenyl optionally substituted with at least one member of the group consisting of halogen, nitro, methyl and methoxy.

27. A method of claim 24 wherein the compound is selected from the group consisting of ethyl 2-oxo-4-phenyl-2H-pyrimido[2,1-b]benzothiazole-8-acetate and its non-toxic, pharmaceutically acceptable salts.

28. A method of claim 24 wherein the compound is selected from the group consisting of ethyl 2-oxo-4-(p-methoxyphenyl)-2H-pyrimido[2,1-b]benzothiazole-8-acetate and its non-toxic, pharmaceutically acceptable salts.

29. A method of claim 24 wherein the compound is selected from the group consisting of ethyl 2-oxo-4-(o-chlorphenyl)-2H-pyrimido[2,1-b]benzothiazole-8-acetate and its non-toxic, pharmaceutically acceptable salts.

30. A method of claim 24 wherein the compound is selected from the group consisting of ethyl α-methyl-2-oxo-4-phenyl-2H-pyrimido[2,1-b]benzothiazole-8-acetate and its non-toxic, pharmaceutically acceptable salts.

31. A method of claim 24 wherein the compound is selected from the group consisting of ethyl α-methyl-2-oxo-4-(p-chlorophenyl)-2H-pyrimido[2,1-b]benzothiazole-8-acetate and its non-toxic, pharmaceutically acceptable salts.

32. A method of claim 24 wherein the compound is selected from the group consisting of ethyl α-ethyl-2-oxo-4-phenyl-2H-pyrimido[2,1-b]benzothiazole-8-acetate and its non-toxic, pharmaceutically acceptable salts.

33. A method of claim 24 wherein the compound is selected from the group consisting of 1-methylcyclohexyl α-methyl-2-oxo-4-phenyl-2H-pyrimido[2,1-b]benzothiazole-8-acetate and its non-toxic, pharmaceutically acceptable salts.

34. A method of claim 24 wherein the compound is selected from the group consisting of 1-adamantyl α-methyl-2-oxo-4-phenyl-2H-pyrimido[2,1-b]benzothiazole-8-acetate and its non-toxic, pharmaceutically acceptable salts.

* * * * *